United States Patent
Hornegger

(10) Patent No.: US 7,386,156 B2
(45) Date of Patent: Jun. 10, 2008

(54) METHOD FOR DIGITAL SUBTRACTION ANGIOGRAPHY USING A VOLUME DATASET

(75) Inventor: Joachim Hornegger, Möhrendorf (DE)

(73) Assignee: Siemens Aktiengesellschaft, Munich (DE)

(*) Notice: Subject to any disclaimer, the term of this patent is extended or adjusted under 35 U.S.C. 154(b) by 695 days.

(21) Appl. No.: 10/825,469

(22) Filed: Apr. 15, 2004

(65) Prior Publication Data
US 2004/0258289 A1 Dec. 23, 2004

(30) Foreign Application Priority Data
Apr. 15, 2003 (DE) .................. 103 17 367

(51) Int. Cl.
*G01N 23/201* (2006.01)
*G06K 9/00* (2006.01)
(52) U.S. Cl. ...................... 382/130; 382/131
(58) Field of Classification Search ................ 382/154, 382/285, 130, 131
See application file for complete search history.

(56) References Cited

U.S. PATENT DOCUMENTS

| | | | | |
|---|---|---|---|---|
| 4,870,692 A | * | 9/1989 | Zuiderveld et al. | 382/107 |
| 5,204,919 A | * | 4/1993 | Murakami | 382/263 |
| 5,630,414 A | * | 5/1997 | Horbaschek | 600/428 |
| 5,647,360 A | * | 7/1997 | Bani-Hashemi et al. | 600/425 |
| 5,774,599 A | * | 6/1998 | Muka et al. | 382/254 |
| 5,796,873 A | * | 8/1998 | Deane | 382/254 |
| 6,014,468 A | * | 1/2000 | McCarthy et al. | 382/254 |
| 6,023,495 A | * | 2/2000 | Adler et al. | 378/4 |
| 6,052,476 A | * | 4/2000 | Qian et al. | 382/130 |
| 6,064,775 A | * | 5/2000 | Suzuki et al. | 382/254 |
| 6,075,836 A | * | 6/2000 | Ning | 378/98.12 |
| 6,118,845 A | * | 9/2000 | Simon et al. | 378/62 |
| 6,298,110 B1 | * | 10/2001 | Ning | 378/4 |
| 6,360,021 B1 | * | 3/2002 | McCarthy et al. | 382/254 |
| 6,379,041 B1 | * | 4/2002 | Schuetz et al. | 378/205 |
| 6,754,522 B2 | * | 6/2004 | Keren | 600/431 |
| 6,947,784 B2 | * | 9/2005 | Zalis | 600/425 |
| 6,990,368 B2 | * | 1/2006 | Simon et al. | 600/425 |
| 2003/0053670 A1 | * | 3/2003 | Hauper et al. | 382/130 |

OTHER PUBLICATIONS

Remko van der Weide, Karel J. Zuiderveld, Willem P. Th. M. Mali, Max A. Viergever, "CTA-Based Angle Selection for Diagnostic and Interventional Angiography of Saccular Intracranial Aneurysms" IEEE Transactions on Medical Imaging, vol. 17, No. 5, Oct. 1998, pp. 831-841.*

(Continued)

*Primary Examiner*—Samir Ahmed
*Assistant Examiner*—Stephen R Koziol
(74) *Attorney, Agent, or Firm*—Schiff Hardin LLP

(57) ABSTRACT

In a method to implement digital subtraction angiography, an image of structures (in particular vessels) of a body region is generated by subtraction of image data of a first 2D x-ray image, that is created without enrichment of the structures with contrast agent, from image data of a second 2D x-ray image of the body region that is acquired with contrast agent enrichment of the structures. The image data of the first 2D x-ray image are calculated from a 3D volume dataset of the body region. The x-ray dose applied in the subtraction angiography thus can be reduced.

3 Claims, 1 Drawing Sheet

OTHER PUBLICATIONS

John Pawasauskas, "Volume Visualization with Ray Casting" http://web.cs.wpi.edu/~matt/courses/cs563/talks/powwie/p1/ray-cast.htm, Feb. 18, 1997.*

2D-3D Rigid-Body Registration of X-Ray Fluoroscopy and CT Images, Lilla Zollei, Department of Electrical Engineering and Computer Science, Massachusetts Institute of Technology, Aug. 2001.*

* cited by examiner

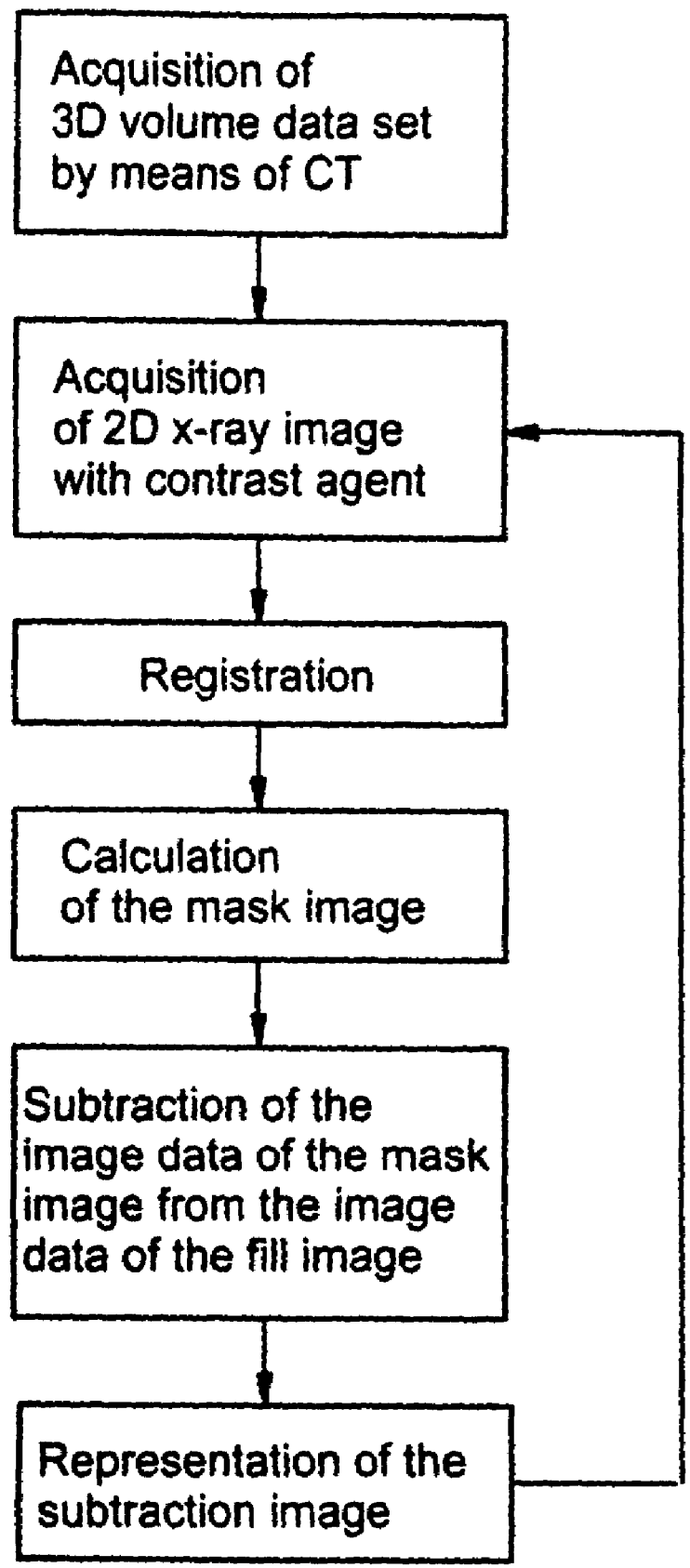

METHOD FOR DIGITAL SUBTRACTION ANGIOGRAPHY USING A VOLUME DATASET

FIELD OF THE INVENTION

The present invention concerns a method to implement digital subtraction angiography of the type wherein an image of structures (in particular vessels) of a body region is generated by subtraction of image data of a first 2D x-ray image, that is created without enrichment of the structures with contrast agent, from image data of a second 2D x-ray image of the body region that is acquired with contrast agent enrichment of the structures.

DESCRIPTION OF THE PRIOR ART

Subtraction angiography is used in particular for representation of vessels of the human body in order to be able to detect possible vessel anomalies such as vessel narrowings (stenoses) or vessel widenings (aneurysms). For better visibility of the vessels in x-ray images, the blood is enriched before the x-ray acquisition with a contrast agent, such that the vessel clearly stands out from (contrasts with) the background. In addition to blood vessels, other structures or objects (for example, bones) also are normally visible in the x-ray image and can partially occlude the vessels in the image. To prevent this problem, the technique of subtraction angiography is used. In subtraction angiography, two digital x-ray exposures of the same body region are acquired from the same projection direction. One of the two exposures, known as the mask image, is implemented without contrast agent; the other exposure, what is known as the fill image, is implemented with contrast agent. The anatomical background identical in the exposures disappears upon subtraction of the digital image data of both exposures that are acquired from logarithmic measurement values of the x-ray detector, such that a pure vessel image results in which even vessels in front of or behind objects such as bones are shown in the image without grey value discontinuities (see "Imaging Systems for Medical Diagnostics", ed.: Erich Krestel, Siemens Aktiengesellschaft, Berlin and Munich, 1990, pp. 369-374).

A disadvantage of this known technique is that two x-ray exposures, a filling exposure and a mask exposure, must be acquired prior to the implementation of the subtraction angiography. These exposures must be made anew upon each of the monitoring examinations that are frequently necessary at regular temporal intervals. This requires that the examination subject be subjected to an x-ray dose for each exposure at each interval.

SUMMARY OF THE INVENTION

An object of the present invention is to provide a method for digital subtraction angiography wherein the x-ray dose for the patient that is necessary for the subtraction angiography is reduced in the long term.

The above object is achieved in accordance with the present invention in a method for digital subtraction angiography wherein an image of structures of a body region is generated by subtracting an image data set of a first 2D x-ray image, generated without enrichment of the structures with contrast agent, from image data of a second 2D x-ray image of the body region that is acquired with contrast agent enrichment of the structures, and wherein the image data of the first 2D x-ray image are calculated from a 3D volume dataset obtained by a computed tomography scan of the body region.

In the present method, use is made of the fact that, in many cases, 3D volume data from an x-ray computed tomography exposure, in particular from C-arm CT, already exist. X-ray computed tomography is a special x-ray slice acquisition method in which transverse slice images, meaning images of body slices essentially oriented perpendicular to the body axis, are acquired. For this, the examination volume is irradiated slice-by-slice from a number of angles, such that a three-dimensional volume data set is acquired. 2D x-ray exposures or photo-realistic 2D images are calculated from these 3D volume data by suitable known projection methods. In addition to such images, other image representations, for example of surface structures of objects in the examination volume, also can be calculated from the 3D volume data with the aid of computed tomography.

In the present method, a conventional 2D x-ray exposure of the corresponding body region of the patient is made after contrast agent enrichment of the structures to be represented, in order to acquire image data of the body region with contrast agent enrichment, meaning the fill image. The image data of the same body region without contrast agent enrichment are, however, not acquired from a further 2D x-ray exposure, but instead are calculated in the present method from the already existing 3D volume data. For each volume element (voxel) of the acquired body region, the 3D volume data have a density value that represents the permeability of this voxel to x-ray radiation without the addition of contrast agent. The calculation of the 2D image data from the 3D volume data ensues in a known manner using the x-ray absorption rule with which the density distribution, that is acquired as an x-ray image given irradiation of this body region from the given projection direction, is calculated. This corresponds to the application of a standard method for volume rendering as described, for example, in H. Schumann, W. Müller, "Visualization. Grundlagen und allgemeine Methoden", Springer Verlag, Berlin, 2000, pages 250 through 306. Transfer function and alpha blending are hereby suitable for parameterization. A mask image thus is obtained that can be subtracted in a known manner from the fill image in order to obtain the image of the structures to be represented.

The correct projection direction in the calculation of the mask image is ensured by a registration, meaning the production of a spatial correlation of the coordinate systems of the 2D x-ray exposure for the fill image for the 3D volume data set, such that the image data of the fill image and of the mask image are acquired from the same projection direction. Suitable methods for registration of medical image data are known to those skilled in the art.

Thus, in each examination of the patient in which the vessels or other structures that can be enriched with contrast agent are shown by means of subtraction angiography, with the present method only a 2D x-ray exposure with the administration of contrast agent is necessary to the create a fill image. The mask image is calculated from already existing 3D volume data. If, at the time the fill image is to be obtained, no 3D volume data exists, it can be acquired before administering the contrast agent. Since a patient normally must be examined at regular intervals, given each further subtraction angiography the 3D volume data that represent the anatomical background can be accessed for each subsequent subtraction. In this case, the present method also leads to a dose reduction for the patient in the long term, meaning after a number of such examinations.

Since the projection directions can be freely predetermined in the calculation of the mask image, the further 2D x-ray exposures to generate fill images need not ensue from the same projection direction. By the registration of each 2D x-ray exposure, it is ensured that the correct mask image can respectively be calculated from the 3D volume data for each fill image from an arbitrary projection direction.

DESCRIPTION OF THE DRAWINGS

The single figure shows an exemplary flow chart given the implementation of the present method to represent blood vessels of the patient.

DESCRIPTION OF THE PREFERRED EMBODIMENTS

As shown in the figure, 3D volume dataset of the patient or at least one body region of the patient is first generated. The acquisition of this data set can either ensue with an x-ray computed tomography apparatus or with an angiography apparatus. It is important that the vessels in this 3D exposure are not enriched with contrast agent, so that the anatomical background for an arbitrary projection direction can be reconstructed from the volume data. The 3D volume data are stored in a known manner and prepared for a later further processing.

In the implementation of the subtraction angiography according to the present method, from the desired viewing or, projection direction, the doctor makes a 2D x-ray exposure of the body region of interest in which the vessels are enriched with contrast agent in order to acquire a fill image.

The 3D volume dataset and the 2D x-ray exposure are registered using a suitable digital image processing technique, such that an exact association of the projection direction of the 2D x-ray exposure with the 3D volume data occurs. If the 3D volume data originate from the exposures of a C-arm apparatus, the implementation of the registration is made easier since the angulation of the C-arm can be used for initial estimation of the projection direction.

A projection coinciding with the 2D x-ray exposure is subsequently calculated from the 3D volume data as a mask image that, lacking contrast agent enrichment, shows only the anatomical background. After a logarithmization of the data (if necessary), the subtraction of the image data of the calculated mask image and acquired fill image provides the desired angiography image.

The first step of the acquisition of a 3D volume data must be implemented only once for the patient. The further steps (for example during a surgical intervention) can be generated arbitrarily often from freely selectable projection directions. Instead of a mask exposure and a fill exposure, in the present method only one 2D x-ray exposure must be implemented, to generate the fill image. A reduction of the x-ray dose and an optimization of the workflow for the medical personnel thus result.

Although modifications and changes may be suggested by those skilled in the art, it is the intention of the inventor to embody within the patent warranted heron all changes and modifications as reasonably and properly come within the scope of this contribution to the art.

I claim as my invention:

1. A method for digital subtraction angiography comprising the steps of:
    providing a 3D volume dataset, obtained from a computed tomography scan of a body region containing structures without enrichment of the structures with a contrast agent;
    from said 3D volume dataset, calculating a first 2D x-ray image of said body region without enrichment of said structures with contrast agent;
    generating a second 2D x-ray image of said body region with contrast agent enrichment of said structures; and
    subtracting said first 2D x-ray image from said second 2D x-ray image.

2. A method as claimed in claim one comprising generating said 3D dataset by conducting said computed tomography scan of said body region with a C-arm CT apparatus.

3. A method as claimed in claim one comprising bringing said second 2D x-ray image into registration with said 3D volume set by digital image processing.

* * * * *